United States Patent [19]

Godfroid et al.

[11] 4,218,473
[45] Aug. 19, 1980

[54] DERIVATIVES OF 4-CYCLOHEXYL-1-NAPHTHALENE-ACETIC ACID AND THEIR USE AS DRUGS

[75] Inventors: Jean-Jacques Godfroid; Efröim Steiner, both of Paris, France

[73] Assignee: Centre Europeen de Recherches Mauvernay, Riom, France

[21] Appl. No.: 945,891

[22] Filed: Sep. 26, 1978

[30] Foreign Application Priority Data

Oct. 3, 1977 [FR] France ............................... 77 29728

[51] Int. Cl.² .............................................. A01N 9/00
[52] U.S. Cl. ................................... 424/317; 560/100; 562/490; 424/308; 260/465 D
[58] Field of Search ........................ 562/490; 560/100; 424/308, 317

[56] References Cited

U.S. PATENT DOCUMENTS 3,904,682  9/1975  Fried et al. ........................ 562/490

FOREIGN PATENT DOCUMENTS 7722244  1/1979  France.

Primary Examiner—Jane S. Myers

Attorney, Agent, or Firm—Haseltine, Lake & Waters

[57] ABSTRACT

The present invention relates to derivatives of 4-cyclohexyl-1-naphthalene-acetic acid of formula

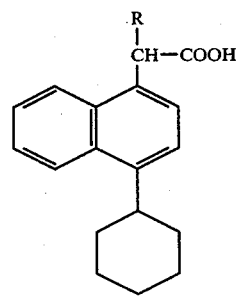

wherein R is a lower alkyl group and pharmaceutically acceptable salts and derivatives thereof the invention also relates to pharmaceutic compositions containing such derivatives.

These derivatives are useful as drugs, notably for the treatment of inflammatory syndromes.

6 Claims, No Drawings

DERIVATIVES OF 4-CYCLOHEXYL-1-NAPHTHALENE-ACETIC ACID AND THEIR USE AS DRUGS

The present invention relates to new derivatives of naphthalene-acetic acid. It also concerns a process for the preparation of these derivatives and their use as drug, notably for the treatment of inflammatory syndromes.

Derivatives of naphthalene-acetic acid are already known. For this purpose, reference may be made to the article of W. E. BACHMANN and L. H. KLEMM [J. Am. Chem. Soc. 72, 4911-15 (1950)] which notably discloses 4-cyclopentyl-1-naphtalene-acetamide. Other derivatives of naphthaleneacetic acid, namely 4-aryl and 5-aryl-1-naphthalene-acetic acids are disclosed in Journal of Medicinal Chemistry, 1973, vol. 16 n°5; these aryl derivatives are anti-inflammatory agents.

French patent application 77 22 244 discloses and covers 4-cyclohexyl-1-naphthaleneacetic acid, which has the following formula:

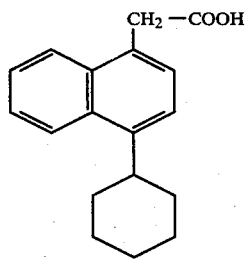

Now it has been found new derivatives of naphthalene acetic acid of formula I; these derivatives are of general formula:

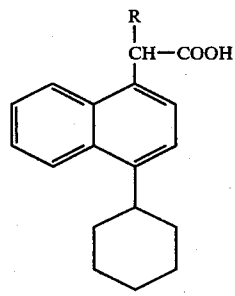

wherein R is a low alkyl group.

Consequently, the present invention concerns the compounds of above formula II; it also includes the pharmaceutically acceptable salts and derivatives of the acids of above formula II.

The present invention also relates to a process for obtaining the compounds of formula II from 4-cyclohexyl-1-naphthaleneacetic acid.

This process comprises the steps of blocking the acid function of 4-cyclohexyl-1-naphthaleneacetic acid by means of an appropriate agent, for example with acetyl chloride, of treating then the resulting compound with the alkyl iodide of formula RI and of liberating the acid function of the thus obtained compound by saponification and thereafter acidification.

4-cyclohexyl-1-naphthaleneacetic acid used as starting material in the process of the present invention may be obtained according to the method disclosed in FR patent 77 22 244; this method comprises the steps of chloro-methylation of 1-cyclohexyl-naphthalene on the carbon atom of naphthalene ring in para position with regard to the cyclohexyl group, of treatment of the chlorinated compound thus obtained by means of an alkaline cyanate, such as KCN or NaCN, then of conversion of the obtained nitrile into the corresponding acid by conventional methods.

This method is illustrated by the reaction scheme as follows:

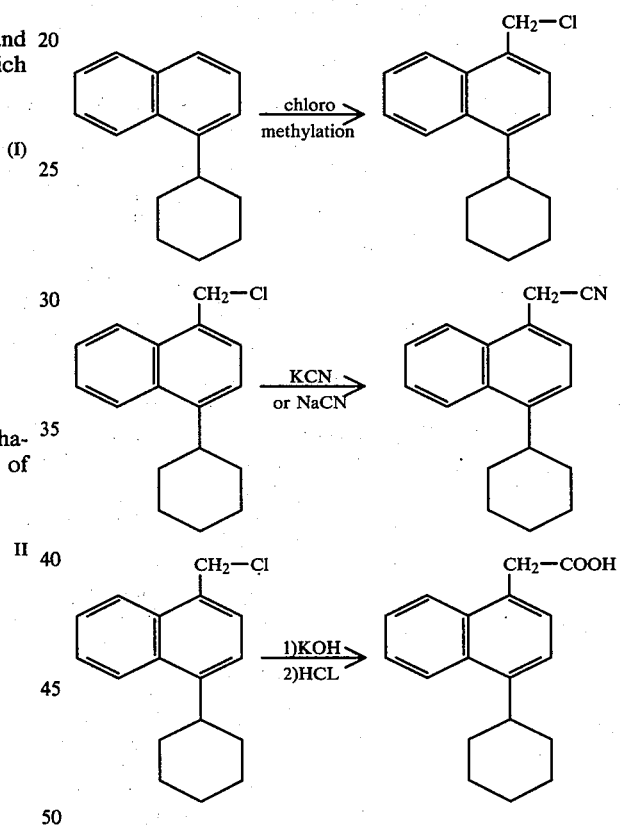

The process for obtaining the compounds of the present invention is illustrated by the following reaction scheme:

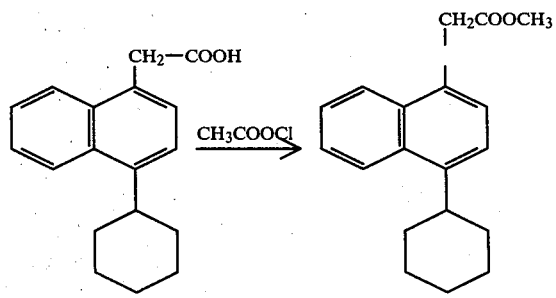

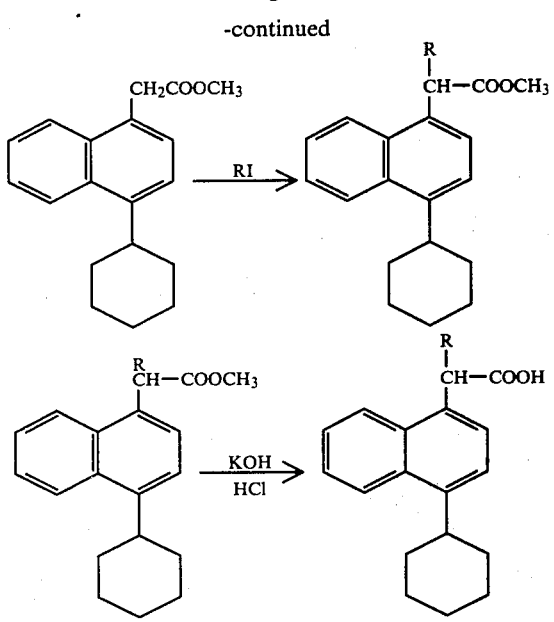

The reaction conditions of the process of the present invention are indicated below by means of an illustrating but non-limiting example.

EXAMPLE

A-Preparation of 4-cyclohexyl-1-naphtaleneacetic acid (starting material)

1-Preparation of 1-chloromethyl-4-cyclohexylnaphthalene.

A mixture of 8 g (0.038 mole) of 1-cyclohexylnaphthalene, 8 g (0.25 mole) of paraformaldehyde, 12 ml of concentrated HCl and 5 ml of $H_3PO_4$ was heated at 85° C. for two hours before adding of additional 3 ml of concentrated HCl and continuing the heating for further 8 hours.

The formed product was extracted with chloroform, washed with water and then with a potassium carbonate solution and further with water. The solvent was evaporated, the residue was taken up with petroleum ether, filtered and the obtained filtrate was evaporated to dryness and the resulting residue was recrystallized from hexane. Thus, 6 g of a product having a melting point of 84° C. was obtained.

Analysis: $C_{17}H_{19}Cl$ Calculated %: C: 78.92; H: 7.35; Cl: 13.73; found %: C: 79.00; H: 7.54; Cl: 13.61.

2-Preparation of 4-cyclohexyl-1-naphthaleneacetonitrile.

A solution of 10 g (0.04 mole) of the above obtained product in 50 ml of acetone and 50 ml of ethanol was treated with 2 g of NaCN solubilized in 15 ml of water by heating with reflux for 5 hours. The reaction mixture was cooled, the solvents were evaporated and the residue was taken up with chloroform, washed with water, dried and recrystallized in hexane.

7.5 g of a product having a melting point of 93° C. was obtained.

Analysis: $C_{18}H_{19}N$ Calculated %: C 86.75; H 7.63; N 5.62; found %: C 86.83; H 7.56; N 5.58.

3. Obtention of 4-cyclohexyl-1-naphthaleneacetic acid.

A solution of 6 g (0.025 mole) of the compound obtained in the preceeding step in 50 ml of ethanol was treated with 6 g of potassium hydroxide in 12 ml of water with reflux for 10 hours.

After cooling and solvent evaporation, the residue was taken up with water and washed with ether. The aqueous phase was then acidified with HCl 6 N. After cooling and filtering, the residue was recrystallized from acetic acid.

Then 4.7 g of 4-cyclohexyl-1-naphthaleneacetic acid having a melting point of 161°-163° C. was obtained.

Analysis: $C_{18}H_{20}O_2$ Calculated %: C 80.60; H 7.46; Found %: C 80.09; H 7.22.

B. Preparation of 2-(4-cyclohexyl-1-naphthyl)propionic acid (compound of formula II wherein R=$CH_3$)

1. Preparation of methyl 4-cyclohexyl-1-naphthylacetate.

To a solution in 80 ml of absolute methanol of 8 g of 4-cyclohexyl-1-naphthylacetic acid (0.03 mole) obtained according to method disclosed under item A were slowly added 5 ml of acetyl chloride freshly distilled. The solution was standing over the night; it was evaporated to dryness and taken up with dichloromethane and then passed through a silica column ("Kieselgel 60", 0.210-0.062 mm) with dichloromethane as eluent. After solvent evaporation 7.6 g of methyl 4-cyclohexyl-1-naphthylacetate were obtained.

Boiling point: 240° C./17 mm Hg
Melting point: 58° C.
Yield: 90%
Analysis: $C_{19}H_{22}O_2$ Calculated %: C: 80.85; H: 7.80; Found % C: 80.87; H: 7.89.

2-Preparation of methyl 2-(4-cyclohexyl-1-naphthyl)-propionate.

A solution of 30 ml of diisopropylamine and 20 ml of tetrahydrofurane (T.H.F.) was cooled to −30° C. under a nitrogen stream. Then a solution of 34 ml (1.2 mole/l) of propyl-lithium (40 millimoles) in T.H.F. was added. After stirring for 30 minutes, 5.65 g (0.02 mole) of methyl 4-cyclohexyl-1-naphthylacetate were added and then, after two hours, 2 ml of methyl iodide in 6 ml of hexamethylphosphorotriamide were added. The stirring and cooling were maintained for 4 hours. The solution was hydrolysed with 50 ml of 10% HCl. The reaction mixture was extracted with ether, washed with sodium thiosulphate and the solvent was evaporated. The residue was passed through a silica column with a mixture of chloroform (33%) and of carbon tetrachloride (66%) as eluent. The single product which passed through the column was evaporated to dryness. 5.5 g of methyl 2-(4-cyclohexyl-1-naphthyl)-propionate were recovered.

Boiling point: 250° C.
Yield: 93%
Analysis: $C_{20}H_{24}O_2$ Calculated % C: 81.08; H: 8.11; Found % C: 80.97; H: 8.17.

3. Preparation of 2-(4-cyclohexyl-1-naphthyl)-propionic acid (compound of the title)

4.44 g (0.015 mole) of methyl 2(4-cyclohexyl-1-naphthyl)-propionate were solubilized in 50 ml of ethyl alcohol and 50 ml of water under heating. 2.8 g of KOH in 50 ml of water were then added and the mixture was heated with reflux for 10 hours. The conventional treatment followed by an acidification with diluted HCl and a recrystallization from a mixture of ethyl alcohol/water gave 3.5 g of 2-(4-cyclohexyl-1-naphthyl)propionic acid.

Melting point: 150° C.

Yield: 83%

Analysis: $C_{19}H_{22}O_2$ Calculated % C: 80.85; H: 7.86; Found % C: 80.97; H: 7.92.

The possibility to use the compounds of the invention for the treatment of inflammatory syndromes was shown by different pharmacologic tests and particularly by the following test, comparatively carried out with phenylbutazone, which is usually used as reference compound. The activity of the compounds of the invention was also compared with the one of 4-cyclohexyl-1-naphthyleneacetic acid.

This test comprises the measurement of a possible inhibition exerted by the compound to be tested with regard to the inflammatory tissue proliferation induced by axilar implantation of cotton pellets impregnated with carragheenine [Method of Bush and Alexander-Acta Endocrinologica 35 (11) 268-275 (1960)].

After getting the pellets into position, the animals (male Wister rats having an average weight of 180±20 g) were divided at random into groups of 10 animals. Then, the animals daily received by oral route the product to be tested (or the vehicle only for the control group) for one week. At the end of this period, the animals were sacrified, the formed granulomes were dissected, dried in a drying oven at 56° C. for 48 hours and then weighted.

By comparison with the control group, it is possible to determine the percentage of inhibition for a given dosage of product to be tested; by means of a series of measures with different dosages, the $ED_{20}$ is calculated, i.e. the daily dosage in mg/kg which allows the 20% reduction of inflammatory tissue proliferation.

The determination of LD 50 by oral route in rats with the compounds of the invention and with phenylbutazone allows the establishment of a table allowing the calculation of the therapeutic index:

$I_{th} = LD\ 50\ /ED\ 20$

TABLE

| | $ED_{20}$ (mg/kg) | LD 50 | $I_{th}$ |
|---|---|---|---|
| Compound according to FR patent 77 22 244 (Formula I) | 60 | 715(1) | 11.9 |
| Compound of the invention (Formula II R=$CH_3$) | 20 | 400(1) | 20 |
| Phenylbutazone | 160 | 650(2) | 4.1 |

(1)Researched and calculated by the method of BERHENS andKARBER [Arch. Exp. Path. Pharm. 177, 379 (1935)].
(2)According to KIMURA G.T. et al. [Arch. Int. Pharmacodyn 202, 119(1973)].

With regard to the secondary effects, it was observed that the compounds of the invention have an ulcerogenic action far lower than the one of phenylbutazone.

Due to these properties, the compounds of the invention may be used for the treatment of inflammatory diseases, by administering under the conventional pharmaceutical forms, for example those suitable for oral administration at the daily dosages which may be comprised between 250 mg and 2 g.

In the pharmaceutical compositions, the new compounds of the invention may be associated with a conventional vehicule, in order to be for example in the form of tablets, syrup, capsules and another known presentation forms.

Generally, the compounds of the invention are used in the acid form. However, their pharmaceutically acceptable salts may be used, particularly their alkaline or earth-alkaline salts.

What we claim is:

1. Derivatives of naphthalene acetic acid of formula:

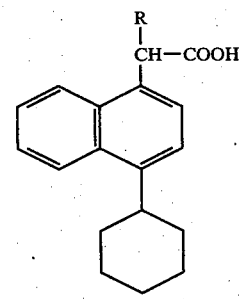

wherein R is a lower alkyl group and their pharmaceutically acceptable salts and methyl ester thereof.

2. Derivative according to claim 1, which is 2-(4-cyclohexyl-1-naphthyl)-propionic acid.

3. Pharmaceutical anti-inflammatory composition comprising an anti-inflammatory effective amount of a compound according to claim 1 in a pharmaceutically acceptable carrier.

4. Pharmaceutical composition according to claim 3, which is suitable for oral administration.

5. Pharmaceutical composition according to claim 3, wherein the compound present in an anti-inflammatory effective amount is 2(4-cyclohexyl-1-naphthyl)-propionic acid.

6. Method of treatment of patients having inflammatory syndromes which comprises the administration of an anti-inflammatory effective amount of a compound according to claim 1 in a pharmaceutical carrier.

* * * * *